United States Patent [19]

Juguin et al.

[11] 4,085,157
[45] Apr. 18, 1978

[54] NEW CATALYSTS FOR HYDROCARBON CONVERSION TO AROMATICS

[75] Inventors: Bernard Juguin, Rueil-Malmaison; Jean Cosyns, Nanterre; Jean-François LePage, Rueil-Malmaison; Jean Miquel, Paris, all of France

[73] Assignee: Societe Francaise des Produits pour Catalyse, Rueil-Malmaison, France

[21] Appl. No.: 770,712

[22] Filed: Feb. 22, 1977

Related U.S. Application Data

[62] Division of Ser. No. 620,410, Oct. 7, 1975, Pat. No. 4,043,944.

[30] Foreign Application Priority Data

Oct. 11, 1974 France .................. 74 34392

[51] Int. Cl.$^2$ .................. C07C 3/03; C10G 35/06; B01J 27/06; B01J 23/48
[52] U.S. Cl. .................. 260/673; 208/139; 252/442; 252/466 PT; 260/668 D; 260/673.5
[58] Field of Search .................. 260/673, 673.5, 668 D; 208/134, 139

[56] References Cited

U.S. PATENT DOCUMENTS

| | | | |
|---|---|---|---|
| 2,911,357 | 11/1959 | Myers et al. | 208/138 |
| 3,692,694 | 9/1972 | Kravitz et al. | 208/111 |
| 3,801,498 | 4/1974 | Rausch | 208/139 |
| 3,856,660 | 12/1974 | Myers | 208/138 |
| 3,892,657 | 7/1975 | Wilhelm | 208/139 |
| 3,901,827 | 8/1975 | Sinfelt et al. | 252/455 R |
| 3,915,846 | 10/1975 | Wilhelm | 208/139 |
| 3,933,622 | 1/1976 | Mitchell et al. | 208/139 |
| 3,939,059 | 2/1976 | Antos | 208/139 |

*Primary Examiner*—Delbert E. Gantz
*Assistant Examiner*—G. E. Schmitkons
*Attorney, Agent, or Firm*—Millen & White

[57] ABSTRACT

Hydrocarbons are dehydrocyclized to aromatics over a new catalyst comprising a carrier such for example as alumina, platinum, at least one metal selected from iridium, tungsten and ruthenium, cobalt, at least one metal selected from the group consisting of copper, manganese, silver and gold, and at least one halogen such for example as chlorine.

11 Claims, No Drawings

NEW CATALYSTS FOR HYDROCARBON CONVERSION TO AROMATICS

This is a division of application Ser. No. 620,410, filed Oct. 7, now U.S. Pat. No. 4,043,944.

This invention concerns a new catalyst containing (a) a carrier, (b) platinum, (c) at least one metal selected from iridium, rhodium and ruthenium, (d) cobalt, (e) at least one other metal selected from the group consisting of copper, manganese, silver and gold and, (f) halogen.

The catalyst of the invention can be used in particular, in the reaction for producing aromatic hydrocarbons of high purity.

By the production of aromatic hydrocarbons, there is meant, for example, the production of benzene, toluene and xylenes (ortho, meta or para), either from unsaturated or saturated gasolines, for example, pyrolysis cracking gasolines, particularly those obtained by steam cracking or catalytic reforming, or still from naphthenic hydrocarbons, convertible, by dehydrogenation, to aromatic hydrocarbons, or also from paraffinic hydrocarbons convertible to aromatic hydrocarbons by dehydrocyclization.

In the case where aromatic hydrocarbons are produced from gasolines, either saturated or unsaturated, it is generally possible to proceed in the manner described below, by way of a non-limitative example:

First of all, in the case of an unsaturated charge, i.e. a charge containing diolefins and monoolefins, the latter must be first removed from the charge for example by selective hydrogenation (the diolefins and alkenylaromatics being converted to monoolefins and alkylaromatics respectively), optionally followed, after a suitable treatment of the effluent, by hydrogenation-hydrodesulfurization, whereby the monoolefins are converted to paraffins and the charge is desulfurized. The charge, thus made substantially free from diolefins and monoolefins, when initially present therein, is fed to at least one reaction zone where it is subjected to a hydrogen treatment in the presence of a catalyst which, up to now, contained a metal from group VIII and/or also a metal or compound of metal from groups VI.B and VII.B of the periodic classification of elements (for example platinum, nickel, cobalt, palladium, iridium, ruthenium, rhenium, tungsten and molybdenum, either sulfurized or not), at a temperature from about 400° to 600° C, under a pressure from 1 to 60 kg/cm$^2$, the hourly flow rate by volume of the liquid charge being from 0.1 to 10 times the catalyst volume, the molar ratio hydrogen/hydrocarbons being from 0.5 to 20. The treatment with hydrogen may be conducted in one or more reaction zones, the catalyst being, generally, a bifunctional catalyst, i.e. a catalyst having an acid function (due to the carrier) and a dehydrogenating function; the acid function is obtained by means of acid compounds such as aluminas and chlorinated and/or fluorinated aluminas, or other similar compounds among which we can mention silica-alumina, silica-magnesia, silica-thoria, alumina-magnesia etc.. The dehydrogenating function is obtained by using metals from groups VIII, VI.B or VII.B of the periodic classification of elements.

In the case where aromatic hydrocarbons are produced from a charge consisting of naphthenic and/or paraffinic hydrocarbons, this charge can be treated under well-known conventional conditions; it can also be treated substantially according to the same operating manner as indicated above, with the optional use, for example, of the same type of catalyst. The treatment with hydrogen may be conducted in one or more reaction zones.

For this type of reaction producing aromatic hydrocarbons, it has been known for a long time to use catalysts containing platinum deposited on a carrier. But, in spite of many recent improvements of these catalysts, for example by incorporation of such additives as tungsten, molybdenum, rhenium, germanium, iridium, etc . . . . there is still to-day a need for new catalysts based on platnium which, on one hand, would give still better yields than those obtained up to now, and which, on the other hand, would also have a longer life time than the known catalysts. Moreover, there is also a need to improve the mechanical properties of such catalysts because they are usually employed in a fixed or moving bed, in the form of conglomerates, for example balls or extrudates, of a substantial size, so as to leave a relatively easy passage to the gaseous reactants, wear of these catalysts results in the formation of much smaller particles which progressively obstruct the free space between the other catalyst particles resulting in the need for an increased inlet pressure of the reactants or even the discontinuance of one operation.

Although it was known that high yields in the production of aromatic hydrocarbons were obtained by making use of a catalyst comprising a porous carrier (mainly alumina) containing simultaneously platinum and another metal from group VIII, it has now been discovered that, in order to obtain aromatic products of very high purity, a catalyst containing platinum and/or iridium, or rhodium, or ruthenium, in even further improved by virtue of an increased activity and also lifetime by the incorporation in the metal system, of both cobalt and a fourth additional metal element selected from copper, manganese, silver and gold. The yields are thus maintained over long periods.

The catalyst of the invention is thus characterized by the two following features:

(a) on the one hand, it contains (1) platinum, (2) another metal from group VIII selected from the group consisting of iridium, rhodium and ruthenium, and (3) cobalt.

During the hydrogen treatment of the charge:
iso, and normal paraffins are cracked mainly to propane, butane and isobutane, to a lesser extent to pentane, isopentane, hexane and isohexane, and additionally to ethane and methane;
naphthenes are dehydrogenated to aromatics and provide the required hydrogen amount for cracking the paraffins;
aromatics are substantially unchanged.

(b) on the other hand, the catalyst also contains critical amounts of at least one other metal selected from the group consisting of copper, silver, gold and manganese. The addition of at least one of the metals considerably decreases the hydrogenolysing and dealkylating powers of the noble metals and consequently makes it possible to increase the aromatic content and to increase the yield of hydrogen produced by dehydrogenation of the naphthenes.

The catalyst of the invention thus contains (a) a carrier, (b) platinum, (c) at least one metal selected from the group consisting of iridium, rhodium and ruthenium, (d) cobalt, (e) an additional metal selected from the group consisting of copper, manganese, silver and gold and (f) at least one halogen, for example chlorine or fluorine.

The carrier comprises at least one oxide of an element from groups II, III and IV of the periodic classification of elements. We will mention for example, alumina, silica, silica-alumina, magnesia, silica-magnesia, alumina-magnesia, silica-thoria, etc.

A particularly suitable carrier is alumina.

The catalyst of the invention preferably contains, by weight with respect to the catalyst carrier, 0.005 to 2 % and more particularly, 0.05 to 1 % of platinum, 0.005 to 1 % and more particularly, 0.02 to 0.1 % of iridium or rhodium or rhutenium, 0.05 to 0.8 % and, more particularly, 0.1 to 0.4 % of cobalt, 0.005 to 1 % of one additional metal selected from copper, manganese, silver and gold. Preferably, the catalyst contains 0.02 to 0.05 % of copper in the case where copper is used and, preferably, in the case of use of manganese, the catalyst contains from 0.1 to 0.2 % of manganese.

The catalyst also contains 0.1 to 10 % and preferably 0.2 to 5 % by weight with respect to the catalyst carrier, of halogen, for example chlorine or fluorine.

The textural characteristics of the catalyst carrier may also be of importance. In order to proceed at high spatial velocities and to avoid the use of reactors of too large a capacity and the use of an excessive amount of catalyst, the specific surface of the carrier will be advantageously in the range from 50 to 600 m$^2$ per gram, preferably from 150 to 400 m$^2$/gram.

It must be noted in the case of several reaction zones, that it may be advantageous to make use of different catalysts in each of said reaction zones. Moreover, irrespective of the number of reaction zones, it may be sometimes advantageous, in order to improve the hydrogen treatment, to divide the treatment conducted in one of the reaction zones into two steps ($\alpha$) and ($\beta$), each of these two steps being conducted in a different reaction zone.

Step ($\alpha$) may be performed at a temperature from about 400° to 600° C, under a pressure preferably from 1 to 60 kg/cm$^2$ in the presence of hydrogen and of a catalyst.

Step ($\beta$) may be conducted at a temperature from about 500° to 600° C, under a pressure preferably from 1 to 60 kg/cm$^2$ in the presence of hydrogen and of a catalyst.

The catalyst used in step ($\alpha$) may be substantially neutral and of a specific surface lower than 100 m$^2$/g (the carrier is, for example, gamma-alumina) and the catalyst used for step ($\beta$) is an acid catalyst having a relatively high specific surface (for example, cubic gamma alumina or chlorinated or fluorinated alumina). In these catalysts, the metal elements may be identical or different in each of the steps ($\alpha$) and ($\beta$) and are those proposed according to this invention.

The catalyst may be prepared according to conventional methods consisting of impregnating the carrier by means of solutions of compounds of the metals which are to be introduced. We make use either of a common solution of these metals or of separate solutions for each metal. When we use several solutions, it may be advisable to proceed to intermediary dryings and/or roastings. Usually a final calcination is performed, for example between 500° and 1000° C, preferably in the presence of free oxygen, for example by using an air scavenging step.

As examples of cobalt, copper, gold, silver and manganese compounds, we can mention, for example, the nitrates, chlorides, bromides, fluorides, sulfates or acetates of said metals or any other salt of these metals soluble in water or in hydrochloric acid.

Platinum may be used in any known form, for example, as hexachloroplatinic acid, ammonium chloroplatinate, platinum sulfide, sulfate or chloride. Iridium, ruthenium and rhodium may be used in any known form, for example as chlorides, bromides, sulfates or sulfides or still as hexachloroiridic acid, hexabromoiridic acid, hexafluoroiridic acid and other iridium, ruthenium and rhodium compounds.

The halogen may be one of the above-mentioned halogens or may be introduced in the form of hydrochloric acid or hydrofluoric acid, ammonium chloride, ammonium fluoride, gaseous chlorine or hydrocarbon halide, for example $CCl_4$, $CHCl_3$ or $CH_3Cl$.

A first preparation method consists, for example, in impregnating the carrier by means of an aqueous solution of copper, gold, silver and manganese compounds such as nitrate, drying at about 120° C and roasting in air for a few hours at a temperature from 500° to 1000° C, preferably about 700° C; said first impregnation being followed with a second impregnation by means of a solution containing platinum, cobalt and another noble metal (for example by means of a solution of hexachloroplatinic acid and hexachloroiridio acid).

Another method consists, for example, in impregnating the carrier by means of a solution simultaneously containing:
(1) platinum (e.g. hexachloroplatinic acid)
(2) the other noble metal (for example, hexachloroiridic acid)
(3) cobalt,
(4) the one or more additional metals selected from copper, silver, gold and manganese (for example a chloride, bromide, fluoride, sulfate or acetate of the selected metal or still any other salt of the selected metal soluble in water or in hydrochloric acid) and
(5) chlorine or fluorine.

Still another method consists of introducing the metal elements by carrying out as much successive impregnations as the number of metal elements present in the catalyst; for example we introduce:
at first the noble metal other than platinum, by means of a solution containing the same, said step being optionally followed with a drying and a roasting step,
then platinum, by means of a solution containing the same, optionally followed with a drying and a roasting step,
the cobalt,
and finally, the one or more additional metals from the group of copper, gold, silver and manganese, the latter impregnation being followed with a drying and a roasting step at a temperature for example from about 500° to 1000° C.

Of course, the sequential order of the impregnations as above-mentioned is not obligatory and may be different.

The so-obtained catalysts may be used for a number of known reactions of hydrocarbon conversion for which there has been previously proposed to make use of platinum catalysts (e.g. reforming, dehydrogenation, dehydrocyclization, isomerization and hydrocracking reactions), but, in particular, these catalysts are used in the reactions for producing aromatic hydrocarbons (called "Aromizing"), said reactions being usually conducted in the general temperature range from 300° 600° C.

Frequently these catalysts are also used in processes in which several of these above-mentioned reactions take place simultaneously.

The catalyst may be arranged:
(1) either in fixed bed in one or more reactors with the optional possibility to provide for an additional replacement reactor which may be operated when the catalyst is regenerated in one of the fixed bed reactors,
(2) or in one or more fluid bed reactors,
(3) or, and this is often one of the best solutions when it is desired to proceed in a continuous manner over long periods, in a reactor with moving bed; the method (described in the French Pat. No. 2,160,269) consists of circulating the charge and hydrogen through at least one reactor zone containing a catayst, for example in granular form, the catalyst being progressively introduced through one end of the reaction zone and progressively withdrawn from the other end of said reaction zone; then the catalyst progressively withdrawn from the reaction zone is conveyed to a regeneration zone; after its regeneration and reduction in the presence of a hydrogen stream, the catalyst is progressively reintroduced through the end of the reaction zone opposite to that from which the catalyst has been withdrawn, in order to replace the amount of catalyst withdrawn from the reaction zone, thereby maintaining a high substantially constant activity level at each point of the reaction zone.

In this third case where we use a moving bed reactor, the catalyst withdrawal from each moving bed reactor or from all the moving bed reactors, when several of them are used, is carried out "progressively" as above-mentioned. By "progressively", is meant that the catalyst may be withdrawn:

either periodically, for example at a rate of 1/10 to 10 days, by withdrawing at each time a fraction, for example 0.5 to 15 % of the total catalyst amount. However, it is generally possible to withdraw the catalyst at a higher frequency (of the order of a minute or a second for example), the withdrawn amount being proportionally reduced, or in a continuous manner.

The one or more moving bed reactors, as well as the regeneration zone, may be placed in any desired position, for example side by side. It may thus be necessary, several times, to ensure the conveyance of the catalyst from a relatively low point to a relatively high point, for example from the bottom of a reaction zone to the top of the regeneration zone; said conveyance being achieved by means of any known lifting device. Such a device, called "lift", makes use of a fluid for conveying the catalyst, any fluid being convenient, for example, nitrogen or hydrogen, particularly purified hydrogen.

The solid which is thus displaced through the moving bed reactor(s) may be a granulated catalyst containing a convenient carrier; this catalyst may be, for example, in the form of spherical balls of a diameter generally from 1 to 3 mm, preferably from 1.5 to 2 mm, although these values are not limitative. The bulk density of the catalyst may be for example from 0.4 to 1, preferably from 0.5 to 0.9 and, more particularly from 0.6 to 0.8, although these values are not limitative.

The regeneration of the catalyst is achieved by any known means or still according to the method described for example in the French Pat. No. 2,160,269.

A preferred method for the treatment of the charge with hydrogen consists of first passing the charge through at least one fixed bed reactor at a temperature from 480° to 530° C, and then through a moving bed reactor at a temperature from 510° to 580° C.

The charge and the catalyst together, irrespective of the type of catalyst bed used, are subjected to conditions which produce the isomerization and dehydrocyclization of the paraffins and the dehydrogenation of the naphthenes, to give a product of high aromatics content and high octane number.

The reactions producing aromatic hydrocarbons of high purity (Aromizing) are generally conducted at a temperature from about 450° to 580° C, or even 600° C, under a pressure from about 5 to 20 kg/cm$^2$, the hourly velocity of the reaction being from 0.5 to 10 volumes of liquid charge (naphtha distilling in the range from about 60° to 220° C) per volume of catalyst.

After the charge has been treated as above-mentioned, the obtained products are made free, through any convenient known means (for example by stripping) from normally gaseous products. The resulting products may then be subjected to one or more fractionations in order to obtain various cuts containing ethylbenzene, xylenes and $C_9+$ hydrocarbons and a $C_6$ and/or $C_7$ cut containing benzene (benzenic fraction) and/or toluene (toluenic fraction) according to the purpose.

Moreover, it was often necessary, up to now, to use such treatments as extractions or extractive distillations, but such treatments are no longer necessary when the reaction for producing aromatics has been conducted according to the present invention, in the presence of the above-mentioned catalysts.

The examples given below illustrate the invention without however limiting the scope thereof.

EXAMPLE 1 (comparative)

We prepare three catalyst A, B, C. The catalyst carrier consists of alumina balls having a specific surface of 250 m$^2$/g.

These three catalysts have the following compositions by weight (with respect to the carrier):
A: 0.6 % platinum - 0.04 % iridium - 1.2 % chlorine
B: 0.6 % platinum - 0.04 % rhodium - 1.2 % chlorine
C: 0.6 % platinum - 0.04 % ruthenium - 1.2 % chlorine.

Over these three catalysts, we pass, with hydrogen, a charge having the following composition by weight:

| | |
|---|---|
| isopentane + n.pentane | 1.59 % |
| isohexanes + n.hexane | 24.22 % |
| isoheptanes + n.heptane | 42.55 % |
| cyclopentane | 0.13 % |
| methylcyclopentane | 6.72 % |
| cyclohexane | 5.50 % |
| $\Sigma$ $C_7$ naphthenes | 15.81 % |
| $\Sigma$ $C_8$ naphthenes | 0.14 % |
| benzene | 1.68 % |
| toluene | 1.66 % |
| | 100 % |

The operating conditions are as follows:
Pressure : 10 bars
Temperature : 550° C Hourly flow rate of the liquid charge : 3 times the catalyst volume.
Molar ratio hydrogen/charge : 6

The results are reported in Table I which indicates, in relation with the age of the catalyst, the weight content of benzene, toluene, benzene + toluene, as compared to the initial charge, as well as the yield by weight of $C_5^+$ hydrocarbons.

TABLE I

| CATA-LYST | Composition by weight of the product | Age of the catalyst (hours) 30 HOURS | 200 HOURS | 400 HOURS |
|---|---|---|---|---|
| A | Benzene | 23.1 % | 21.2 % | 18.9 % |
|   | Toluene | 31.2 % | 29.7 % | 27.9 % |
|   | Benzene + Toluene | 54.3 % | 50.9 % | 46.8 % |
|   | Yield of $C_5+$ b.w. | 60.5 % | 61.5 % | 63.7 % |
| B | Benzene | 23.9 % | 22.1 % | 19.3 % |
|   | Toluene | 30.5 % | 28.9 % | 26.8 % |
|   | Benzene + Toluene | 54.4 % | 51 % | 46.1 % |
|   | Yield of $C_5$ + b.w. | 59 % | 60.5 % | 63 % |
| C | Benzene | 20.4 % | 18.7 % | 16.8 % |
|   | Toluene | 32 % | 30.4 % | 28.6 % |
|   | Benzene + Toluene | 52.4 % | 49.1 % | 45.4 % |
|   | Yield of $C_5$ + b.w. | 62 % | 63.8 % | 65.5 % |

EXAMPLE 2 (comparative)

We prepare 3 catalyst D, E, F, having the following compositions by weight (with respect to the carrier):

D : 0.6 % platinum - 0.04 % iridium - 0.25 % cobalt - 1.2 % chlorine.
E : 0.6 % platinum - 0.04 % rhodium - 0.25 % cobalt - 1.2 % chlorine.
F : 0.6 % platinum - 0.04 % ruthenium - 0.25 % cobalt - 1.2 % chlorine.

The charge of example 1 is passed over the three catalysts under the same operating conditions as in example 1 and the results are reported in the following table II.

TABLE II

| CATA-LYST | Composition by weight of the product | Age of the catalyst (hours) 30 HOURS | 200 HOURS | 400 HOURS |
|---|---|---|---|---|
| D | Benzene | 25.3 % | 24.2 % | 23 % |
|   | Toluene | 33.4 % | 32.7 % | 31.8 % |
|   | Benzene + Toluene | 58.7 % | 56.9 % | 54.8 % |
|   | Yield of $C_5+$ b.w. | 65.8 % | 66.5 % | 67.6 % |
| E | Benzene | 26 % | 25.1 % | 24 % |
|   | Toluene | 32.9 % | 32.3 % | 31.5 % |
|   | Benzene + Toluene | 58.9 % | 57.4 % | 55.5 % |
|   | Yield of $C_5$ + b.w. | 64.7 % | 65.5 % | 66.4 % |
| F | Benzene | 22.9 % | 22.1 % | 21.2 % |
|   | Toluene | 33.8 % | 33.1 % | 32.3 % |
|   | Benzene + Toluene | 56.7 % | 55.2 % | 53.5 % |
|   | Yield of $C_5$ + b.w. | 67.7 % | 68.6 % | 69.5 % |

When comparing these results to those obtained with catalysts A-B-C, we may observe that the addition of cobalt to the catalysts strongly improves the yields of aromatic hydrocarbons (benzene and toluene), and also the yield by weight of $C_5^+$, which means that the selectivity of the catalysts has been increased.

It can also be observed that the life time of the catalyst is substantially improved.

EXAMPLE 3

We prepare 3 catalysts G, H and I, having the following compositions by weight:

G : 0.6 % platinum - 0.04 % iridium - 0.25 % cobalt - 0.035 % copper - 1.2 % chlorine
H : 0.6 % platinum - 0.04 % rhodium - 0.25 % cobalt - 0.035 % copper - 1.2 % chlorine
I : 0.6 % platinum - 0.04 % ruthenium - 0.25 % cobalt - 0.035 % copper - 1.2 % chlorine.

The charge of example 1 is passed over these 3 catalysts under the same operating conditions as in example 1. The results are reported in table III.

Catalyst G was prepared by adding 100 g of the alumina of example 1 to 100 cc of an aqueous solution containing:
0.134 g of copper nitrate with 3 molecules of water,
2.10 g of concentrated HCl (d = 1.19),
25.50 cc of an aqueous solution of chloroplatinic acid having a platinum content by weight of 2.35 %,
1.74 cc of an aqueous solution of chloroiridic acid having an iridium content of 2.3 % by weight,
1.23 g of cobalt nitrate $CO(NO_3)_2$ — 6 $H_2O$.

The contact is maintained for 5 hours, and the resulting product is centrifuged and dried for 1 hour at 100° C, then roasted at 530° C in dry air (drying with activated alumina). Then, it is reduced under dry hydrogen stream (activated alumina) for 2 hours at 450° C. The resulting catalyst contains by weight with respect to the catalyst carrier:
0.60 % of platinum
0.04 % of iridium
0.25 % cobalt
0.04 % of copper
1.2 % of chlorine
The specific surface of the catalyst is 245 m²/g.

Catalyst H was prepared as catalyst C but with the use of 1.60 g of an aqueous solution of rhodium trichloride having a 2.5 % by weight rhodium content instead of 1.74 cc of chloroiridic acid solution.

Catalyst I was prepared as catalyst C by using 1.60 g of an aqueous solution of ruthenium trichloride with a 2.5 % by weight ruthenium content instead of 1.74 cc of chloroiridic solution.

TABLE III

| CATA-LYST | Composition by weight of the product | Age of the catalyst (hours) 30 HOURS | 200 HOURS | 400 HOURS |
|---|---|---|---|---|
| G | Benzene | 27 % | 26.5 % | 25.9 % |
|   | Toluene | 35.3 % | 34.9 % | 34.4 % |
|   | Benzene + Toluene | 62.3 % | 61.4 % | 60.3 % |
|   | Yield of $C_5+$ b.w. | 71.6 % | 72 % | 72.6 % |
| H | Benzene | 27.6 % | 27.2 % | 26.8 % |
|   | Toluene | 34.6 % | 34.3 % | 33.7 % |
|   | Benzene + Toluene | 62.2 % | 61.5 % | 60.5 % |
|   | Yield of $C_5$ + b.w. | 70.5 % | 70.8 % | 71.4 % |
| I | Benzene | 25.4 % | 25.1 % | 24.6 % |
|   | Toluene | 35.8 % | 35.4 % | 34.8 % |
|   | Benzene + Toluene | 61.2 % | 60.5 % | 59.4 % |
|   | Yield of $C_5$ + b.w. | 72.8 % | 73.2 % | 73.7 % |

When comparing these results to those obtained with catalysts D, E, F, it is observed that the addition of copper very substantially improves the selectivity of the catalyst since the yields of aromatic hydrocarbons are still much increased. The addition of copper particularly improves the stability of the catalysts.

EXAMPLE 4

We prepare 3 catalysts J, K, L having the following composition by weight:

J : 0.6 % platinum - 0.04 % iridium - 0.25 % cobalt - 1.15 % manganese - 1.2 % chlorine
K : 0.6 % platinum - 0.04 % rhodium - 0.25 % cobalt - 0.15 % magnanese - 1.2 % chlorine
L : 0.6 % platinum - 0.04 % ruthenium - 0.25 % cobalt - 0.15 % manganese - 1.2 % chlorine.

The charge of example 1 is passed over these 3 catalysts under the same operating conditions as in this example. The results are given in table IV.

TABLE IV

| CATA-LYST | Composition by weight of the product | Age of the catalyst (hours) | | |
|---|---|---|---|---|
| | | 30 HOURS | 200 HOURS | 400 HOURS |
| J | Benzene | 26.2 % | 25.6 % | 24.9 % |
| | Toluene | 34.6 % | 34.1 % | 33.5 % |
| | Benzene + Toluene | 60.8 % | 59.7 % | 58.4 % |
| | Yield of $C_5$ + b.w. | 68.9 % | 69.4 % | 70.1 % |
| K | Benzene | 26.6 % | 26.1 % | 25.5 % |
| | Toluene | 34 % | 33.6 % | 32.9 % |
| | Benzene + Toluene | 60.6 % | 59.7 % | 58.4 % |
| | Yield of $C_5$ + b.w. | 68 % | 68.4 % | 69 % |
| L | Benzene | 24.3 % | 24 % | 23.4 % |
| | Toluene | 35.1 % | 34.6 % | 34.1 % |
| | Benzene + Toluene | 59.4 % | 58.6 % | 57.5 % |
| | Yield of $C_5$ + b.w. | 71.1 % | 71.6 % | 72.2 % |

By comparing these results to those obtained with catalysts D-E-F, we may observe that the addition of manganese, also improves the selectivity and the life time of the catalysts.

Catalyst J was prepared by adding 100 g of the alumina of example 1 to 100 cc of an aqueous solution containing:
0.70 g of manganese nitrate with 6 moles of water,
2.10 g of concentrated HCl (d = 1.19),
25.50 cc of aqueous solution of chloroplatinic acid with a 2.35 % by weight platinum content,
1.74 cc of aqueous solution of chloroiridic acid with a 2.3 % by weight iridium content,
1.23 g of cobalt nitrate $CO(NO_3)_2$— 6 $H_2O$.

The contact is maintained for five hours, and the obtained product is centrifugated and dried for 1 hour at 100° C, then roasted at 530° C in dry air (drying with activated alumina). Then, it is reduced under a stream of dry hydrogen (activated alumina) for 2 hours at 450° C. The resulting catalyst contains, by weight with respect to the catalyst carrier:
0.60 % of platinum,
0.04 % of iridium,
0.25 % of cobalt,
0.15 % of manganese,
1.2 % of chlorine.

The specific surface of this catalyst is 245 m²/g.

Catalyst K was prepared as catalyst J but using 1.60 g of an aqueous solution of rhodium trichloride with a 2.5 % by weight rhodium content, instead of 1.74 cc of chloroiridic acid solution.

Catalyst L was prepared as catalyst J, but with the use of 1.60 g of an aqueous solution of ruthenium trichloride with a 2.5 % by weight ruthenium content, instead of 1.74 cc of chloroiridic acid solution.

EXAMPLE 5

We prepare 2 catalysts $E_1$ and $E_2$ having the following compositions:
$E_1$: 0.6 % platinum - 0.04 % rhodium - 0.08 % cobalt - 1.2 % chlorine
$E_2$: 0.6 % platinum - 0.04 % rhodium - 0.50 % cobalt - 1.2 % chlorine.

The charge of example 1 is passed over these catalysts in the same operating conditions as in this example. The comparative results of catalysts E and B are reported in table V below.

TABLE V

| CATA-LYST | Composition by weight of the product | Age of the catalyst (hours) | | |
|---|---|---|---|---|
| | | 30 HOURS | 200 HOURS | 400 HOURS |
| B | Benzene | 23.9 % | 22.1 % | 19.3 % |
| | Toluene | 30.5 % | 28.9 % | 26.8 % |
| | Benzene + Toluene | 54.4 % | 51 % | 46.1 % |
| | Yield of $C_5$ + b.w. | 59 % | 60.5 % | 63 % |
| $E_1$ | Benzene | 24.7 % | 23.3 % | 21.2 % |
| | Toluene | 31.5 % | 30.3 % | 28.7 % |
| | Benzene + Toluene | 56.2 % | 53.6 % | 49.9 % |
| | Yield of $C_5$ + b.w. | 61.3 % | 62.5 % | 64.4 % |
| E | Benzene | 26 % | 25.1 % | 24 % |
| | Toluene | 32.9 % | 32.3 % | 31.5 % |
| | Benzene + Toluene | 58.9 % | 57.4 % | 55.5 % |
| | Yield of $C_5$ + b.w. | 64.7 % | 65.5 % | 66.4 % |
| $E_2$ | Benzene | 22.1 % | 21.9 % | 21.6 % |
| | Toluene | 29 % | 28.7 % | 28.4 % |
| | Benzene + Toluene | 51.1 % | 50.6 % | 50 % |
| | Yield of $C_5$ + b.w. | 71 % | 71.9 % | 72.6 % |

The results show that the cobalt content is highly important for the catalyst performances, and that it is preferable to make use of a cobalt content ranging from 0.1 to 0.4 % by weight.

A cobalt content lower than 0.1 % would result in a certain improvement of the catalyst performances (selectivity and stability) but this improvement would be insufficient and a cobalt content of more than 0.4 % by weight would result in a very good stability of the catalyst but in aromatic yields substantially lower due to the loss of activity of the catalyst.

EXAMPLE 6

We prepare 2 catalysts $H_1$ and $H_2$ having the following composition:
$H_1$: 0.6 % platinum - 0.04 % rhodium - 0.25 % cobalt - 0.015 % copper - 1.2 % chlorine
$H_2$: 0.6 % platinum - 0.04 % rhodium - 0.25 % cobalt - 0.07 % copper - 1.2 % chlorine.

The charge of example 1 is passed over these catalysts under the same operating conditions as in said example.

The results obtained with these catalysts are compared to those obtained with catalysts E and H, in table VI below.

TABLE VI

| CATA-LYST | Composition by weight of the product | Age of the catalyst (hours) | | |
|---|---|---|---|---|
| | | 30 HOURS | 200 HOURS | 400 HOURS |
| E | Benzene | 26 % | 25.1 % | 24 % |
| | Toluene | 32.9 % | 32.3 % | 31.5 % |
| | Benzene + Toluene | 58.9 % | 57.4 % | 55.5 % |
| | Yield of $C_5$ + b.w. | 64.7 % | 65.5 % | 66.4 % |
| $H_1$ | Benzene | 26.7 % | 26 % | 25.2 % |
| | Toluene | 33.6 % | 33.1 % | 32.5 % |
| | Benzene + Toluene | 60.3 % | 59.1 % | 57.7 % |
| | Yield of $C_5$ + b.w. | 67.2 % | 67.8 % | 68.6 % |
| H | Benzene | 27.6 % | 27.2 % | 26.8 % |
| | Toluene | 34.6 % | 34.3 % | 33.7 % |
| | Benzene + Toluene | 62.2 % | 61.5 % | 60.5 % |
| | Yield of $C_5$ + b.w. | 70.5 % | 70.8 % | 71.4 % |
| $H_2$ | Benzene | 19.7 % | 19.6 % | 19.1 % |
| | Toluene | 27.8 % | 27.6 % | 27.4 % |
| | Benzene + Toluene | 47.5 % | 47.2 % | 46.8 % |
| | Yield of $C_5$ + b.w. | 76.8 % | 77.1 % | 77.5 % |

The results show that the selection of the copper content is also important and that it is preferable to make use of copper contents in the range from 0.02 to 0.05 % by weight.

EXAMPLE 7

We prepare 2 catalysts $J_1$ and $J_2$ having the following composition:

J₁ : 0.6 % platinum - 0.04 % iridium - 0.25 % cobalt - 0.06 % manganese - 1.2 % chlorine J₂ : 0.6 % platinum - 0.04 % iridium - 0.25 % cobalt - 0.30 % manganese - 1.2 % chlorine.

The charge of example 1 is passed over these catalysts under the same operating conditions as in said example. The results obtained with these catalysts are compared to those obtained with catalysts J and D in table VII below.

TABLE VII

| CATA-LYST | Composition by weight of the product | Age of the catalyst (hours) | | |
|---|---|---|---|---|
| | | 30 HOURS | 200 HOURS | 400 HOURS |
| D | Benzene | 25.3 % | 24.2 % | 23 % |
| | Toluene | 33.4 % | 32.7 % | 31.8 % |
| | Benzene + Toluene | 58.7 % | 56.9 % | 54.8 % |
| | Yield of C₅ + b.w. | 65.8 % | 66.5 % | 67.6 % |
| J₁ | Benzene | 25.7 % | 24.8 % | 23.8 % |
| | Toluene | 33.9 % | 33.3 % | 32.5 % |
| | Benzene + Toluene | 59.6 % | 58.1 % | 56.3 % |
| | Yield of C₅ + b.w. | 67 % | 67.6 % | 68.5 % |
| J | Benzene | 26.2 % | 25.6 % | 24.9 % |
| | Toluene | 34.6 % | 34.1 % | 33.5 % |
| | Benzene + Toluene | 60.8 % | 59.7 % | 58.4 % |
| | Yield of C₅ + b.w. | 68.9 % | 69.4 % | 70.1 % |
| J₂ | Benzene | 20.6 % | 20.4 % | 20.1 % |
| | Toluene | 28.2 % | 27.9 % | 27.7 % |
| | Benzene + Toluene | 48.8 % | 48.3 % | 47.8 % |
| | Yield of C₅ + b.w. | 74.3 % | 74.6 % | 74.9 % |

The results show that the manganese content is also important and that it is preferable to make use of manganese contents in the range from 0.1 to 0.2 % by weight.

We claim:

1. In a process for the production of aromatic hydrocarbon by cyclization, dehydrogenation or dehydrocyclization of an appropriate starting compound over a catalyst, the improvement which comprises employing as said catalyst, a catalyst consisting essentially of (a) a carrier and, expressed in proportion by weight with respect to the carrier, (b) 0.005 to 2% of platinum, (c) 0.005 to 1% of a metal selected from the group consisting of iridium, rhodium and ruthenium, (d) 0.05 to 0.8% of cobalt, (e) 0.005 to 1% of at least one metal selected from the group consisting of copper, manganese, silver and gold, and (f) 0.1 to 10% of at least one halogen.

2. The process of claim 1, wherein the process is conducted in a hydrogen-containing atmosphere and the starting material comprises paraffinic compounds.

3. A process according to claim 1, in which the carrier is alumina.

4. A process according to claim 3, in which the halogen is chlorine.

5. A process according to claim 3, in which the catalyst contains with respect to alumina, 0.02 to 0.1% by weight of a metal selected from the group consisting of iridium, rhodium and ruthenium, and 0.1 to 0.4% by weight of cobalt.

6. A process according to claim 5, in which the catalyst contains (a) alumina, (b) platinum, (c) iridium, (d) cobalt, (e) 0.02 to 0.05% of copper, expressed by weight with respect to alumina, and (f) at least one halogen.

7. A process according to claim 5 in which the catalyst contains (a) alumina, (b) platinum, (c) rhodium, (d) cobalt, (e) 0.02 to 0.05% of copper, by weight with respect to alumina, and (f) at least one halogen.

8. A process according to claim 5 in which the catalyst contains (a) alumina, (b) platinum, (c) ruthenium, (d) cobalt, (e) 0.02 to 0.05% of copper, by weight with respect to alumina, and (f) at least one halogen.

9. A process according to claim 5, in which the catalyst contains (a) alumina, (b) platinum, (c) iridium, (d) cobalt, (e) 0.1 to 0.2% of manganese, by weight with respect to alumina, and (f) at least one halogen.

10. A process according to claim 5, in which the catalyst contains (a) alumina, (b) platinum, (c) rhodium, (d) cobalt, (e) 0.1 to 0.2% of manganese, by weight with respect to alumina, and (f) at least one halogen.

11. A process according to claim 5 in which the catalyst contains (a) alumina, (b) platinum, (c) ruthenium, (d) cobalt, (e) 0.1 to 0.2% of manganese, by weight with respect to alumina, and (f) at least one halogen.

* * * * *